United States Patent
Costello et al.

(10) Patent No.: US 9,414,916 B2
(45) Date of Patent: *Aug. 16, 2016

(54) ADAPTER TO ACTUATE A DELIVERY SYSTEM

(71) Applicant: Medtronic Vascular Galway, Ballybrit, Galway (IE)

(72) Inventors: Declan Costello, Ballybrit (IE); Marc A. Anderson, Ballybrit (IE)

(73) Assignee: Medtronic Vascular Galway, Galway (IE)

( * ) Notice: Subject to any disclaimer, the term of this patent is extended or adjusted under 35 U.S.C. 154(b) by 163 days.

This patent is subject to a terminal disclaimer.

(21) Appl. No.: 13/944,272

(22) Filed: Jul. 17, 2013

(65) Prior Publication Data

US 2015/0025621 A1    Jan. 22, 2015

(51) Int. Cl.
  *A61F 2/24* (2006.01)
  *A61F 2/962* (2013.01)
  *B23B 45/00* (2006.01)
  *A61F 2/95* (2013.01)

(52) U.S. Cl.
  CPC ............... *A61F 2/2436* (2013.01); *A61F 2/962* (2013.01); *B23B 45/00* (2013.01); *A61F 2002/9517* (2013.01)

(58) Field of Classification Search
  CPC ............ A61F 2002/9517; A61F 2/243; A61F 2/2436; A61F 2/95; A61F 2/962; A61F 2002/011; B23B 45/00

USPC ................. 623/1.11, 1.12, 2.11; 606/191, 200
See application file for complete search history.

(56) References Cited

U.S. PATENT DOCUMENTS

| | | | |
|---|---|---|---|
| 2002/0004676 A1* | 1/2002 | Wallace | A61B 17/12118 623/1.12 |
| 2006/0282150 A1* | 12/2006 | Olson | A61F 2/966 623/1.11 |
| 2009/0099638 A1* | 4/2009 | Grewe | A61F 2/966 623/1.11 |
| 2009/0228093 A1 | 9/2009 | Taylor et al. | |
| 2010/0049313 A1 | 2/2010 | Alon et al. | |
| 2012/0022628 A1* | 1/2012 | Dwork | A61F 2/95 623/1.11 |
| 2014/0180381 A1* | 6/2014 | Kelly | A61F 2/966 623/1.11 |
| 2014/0343670 A1* | 11/2014 | Bakis | A61F 2/2436 623/2.11 |

* cited by examiner

*Primary Examiner* — Katherine M Shi

(57) ABSTRACT

Apparatus for actuating a delivery system are disclosed. The apparatus may comprise an adapter. The adapter may comprise an input, a first actuator, and a second actuator. The adapter may be configured to receive a portion of a delivery system. The adapter may be configured to impart translational motion to the delivery system. The adapter may be configured to impart translational motion to a catheter. The adapter may be configured to be actuated by a motorized device or a drill. The adapter may be configured to actuate multiple delivery systems. The adapter may be configured to at least partially compress a portion of an article such as a prosthetic heart valve.

9 Claims, 8 Drawing Sheets

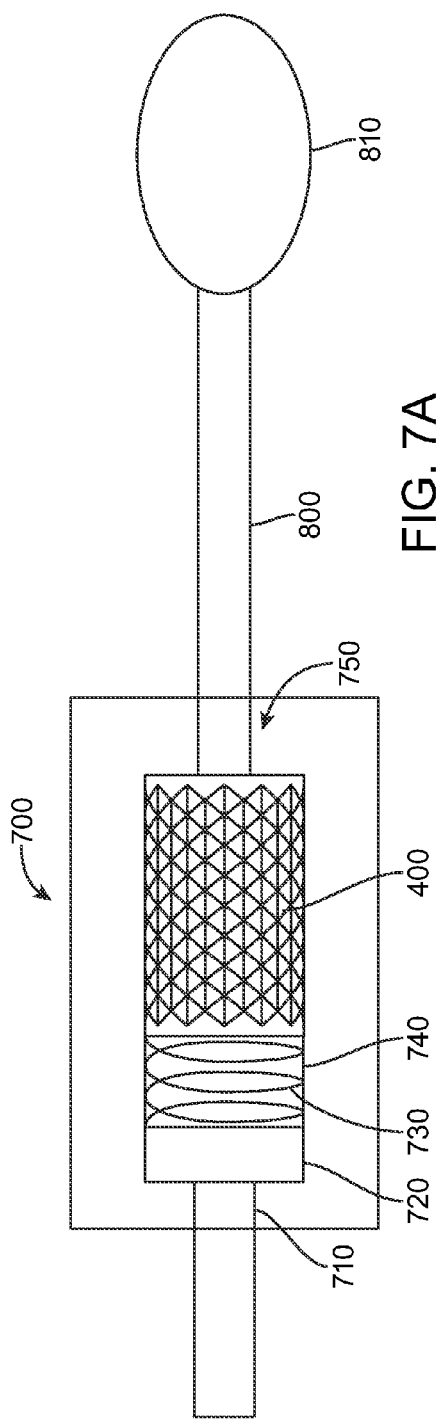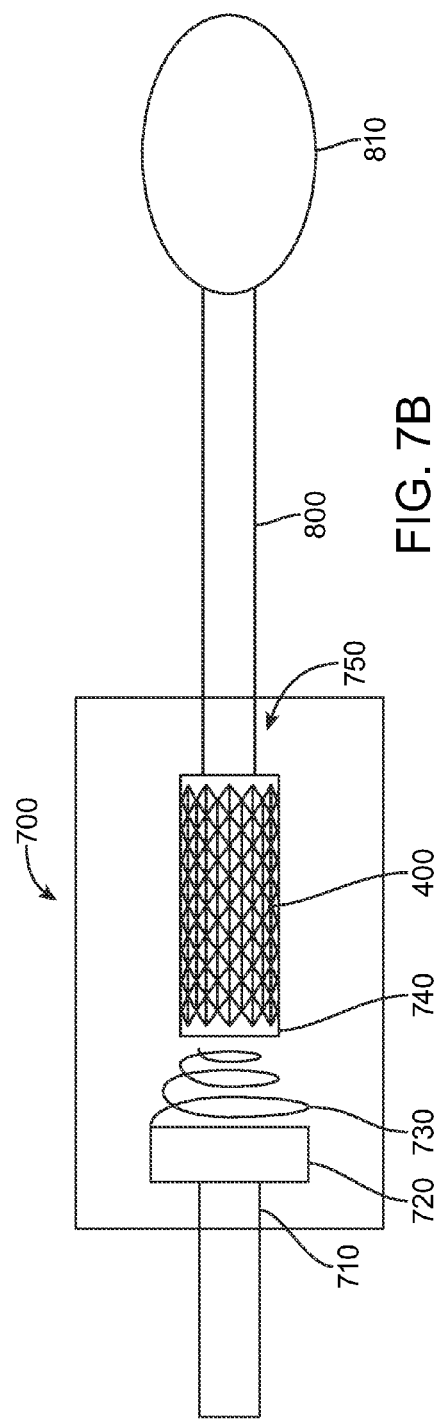

ADAPTER TO ACTUATE A DELIVERY SYSTEM

BACKGROUND

Many procedures exist in which a prosthesis is loaded and deployed on a delivery system or by a delivery system. Some of these prostheses include transcatheter aortic valve implants (TAVI). In some procedures to deploy certain prostheses a physician implants the prosthesis. In some procedures a TAVI is deployed using an electromechanical system. However, such electromechanical systems can be complicated, costly, required disposal of certain parts, and may be subject to multiple health care rules or regulations or other rules and regulations. The drawbacks of using such electromechanical devices can prove costly, inconvenient, and discourage or prohibit physicians from using such systems. But electromechanical systems can provide advantages over non-electromechanical systems. Thus, there is a need to develop an electromechanical system that can load and deploy a prosthetic in such a way that the prosthetic and the system may comply with procedures, while also being safe, efficient, and cost effective.

BRIEF SUMMARY

In accordance with some embodiments an adapter is configured to actuate a delivery system. In some embodiments an adapter may comprise an input shaft, a first actuator, and a second actuator. In some embodiments adapter may comprise a stopper to prevent or limit motion of one or more actuators. In some embodiments an adapter may comprise a torque limiter. In some embodiments an adapter may comprise a gear box. In some embodiments an adapter may comprise opening. In some embodiments a first actuator and a second actuator comprises gears. In some embodiments a first actuator and a second actuator comprises an actuator other than a gear.

In some embodiments an adapter is configured to impart translational motion to a delivery system. In some embodiments an adapter is configured to impart translational motion to a catheter. In some embodiments an adapter is configured to impart translational motion to a portion of catheter, such as a tip.

In some embodiments an adapter is configured to be actuated by a drill device. In some embodiments an adapter is configured to be actuated by a motorized device. In some embodiments an adapter provides a way to utilize an electromechanical system without certain drawbacks associated with such a system.

In some embodiments an apparatus for actuating a delivery system is disclosed, the apparatus comprising an input shaft, a first actuator coupled to the input shaft, and a second actuator configured to be coupled to a first catheter-based delivery system. In some embodiments the first actuator is configured to actuate the second actuator such that a first portion of the first catheter-based delivery system is actuated.

In some embodiments translational motion of the second actuator results from a rotation of the first actuator.

In some embodiments the input shaft is configured to be actuated by a motorized drill.

In some embodiments the apparatus is configured to limit the amount of translational motion of the second actuator by a limit switch.

In some embodiments the apparatus further comprises a first catheter-based delivery system comprising a tip, a capsule adjacent the tip, and an inner sheath adjacent the capsule. In some embodiments the translational motion of the second actuator corresponds to translational motion of the tip of the first catheter-based delivery system.

In some embodiments the apparatus further comprises a torque limiter, wherein the torque limiter is configured to limit an output torque of the apparatus.

In some embodiments the apparatus further comprises a gear box.

In some embodiments the apparatus further comprises a third actuator configured to be coupled to the first catheter-based delivery system. In some embodiments the apparatus further comprises a selector. In some embodiments the first actuator is configured to actuate the third actuator such that a second portion of the first catheter-based delivery system is actuated. In some embodiments the first actuator is configured to actuate the second actuator and the third actuator. In some embodiments when the selector is actuated the first actuator actuates one of the second actuator and the third actuator.

Some embodiments provide a method of actuating a delivery system, the method comprising attaching an electrically-powered apparatus to a catheter-based delivery system, the apparatus comprising an input shaft, a first actuator attached to the input shaft, the first actuator configured to interact with a second actuator, the second actuator coupled to the catheter-based delivery system.

In some embodiments the method may further comprise actuating the input shaft via a power source. In some embodiments the method may further comprise actuating the catheter-based delivery system via the apparatus.

In some embodiments the power source comprises a drill. In some embodiments actuating the catheter-based delivery system comprises advancing the catheter-based delivery system via the actuators actuated by the drill. In some embodiments advancing the catheter-based delivery system further comprises imparting translational movement via the actuators.

In some embodiments the catheter-based delivery system further comprises a channel and a compressor and an article. In some embodiments the channel is configured to receive the article. In some embodiments actuating the catheter-based delivery system comprises compressing a portion of the article.

In some embodiments the catheter-based delivery system further comprises a catheter. In some embodiments the article comprises a heart valve. In some embodiments actuating the catheter-based delivery system comprises compressing the heart valve into a cylindrical shape. In some embodiments the heart valve is disposed on the catheter.

In some embodiments an assembly comprises a first actuator, a second actuator, and a channel. In some embodiments the first actuator is configured to be actuated by a motor. In some embodiments the channel is configured to receive a prosthesis. In some embodiments the channel is configured to compress a portion of the prosthesis via the second actuator. In some embodiments the channel is configured to receive a catheter-based delivery system.

In some embodiments the second actuator comprises a spring.

In some embodiments the second actuator comprises an arm.

In some embodiments the first actuator is configured to be actuated by a drill.

In some embodiments the channel is configured to receive a heart valve and a heart valve frame.

In some embodiments the apparatus further comprises a detachable portion.

In some embodiments the channel is further configured to compress the article into a cylinder via the second actuator.

In some embodiments the article is disposed on the catheter after being compressed into a cylinder.

The embodiments and related concepts will be more fully understood from the following detailed description of the embodiments thereof.

BRIEF DESCRIPTION OF THE FIGURES

FIGS. 7A and 7B illustrate an apparatus for actuating a delivery system in accordance with some embodiments.

DETAILED DESCRIPTION OF EMBODIMENTS

Figure 1A:
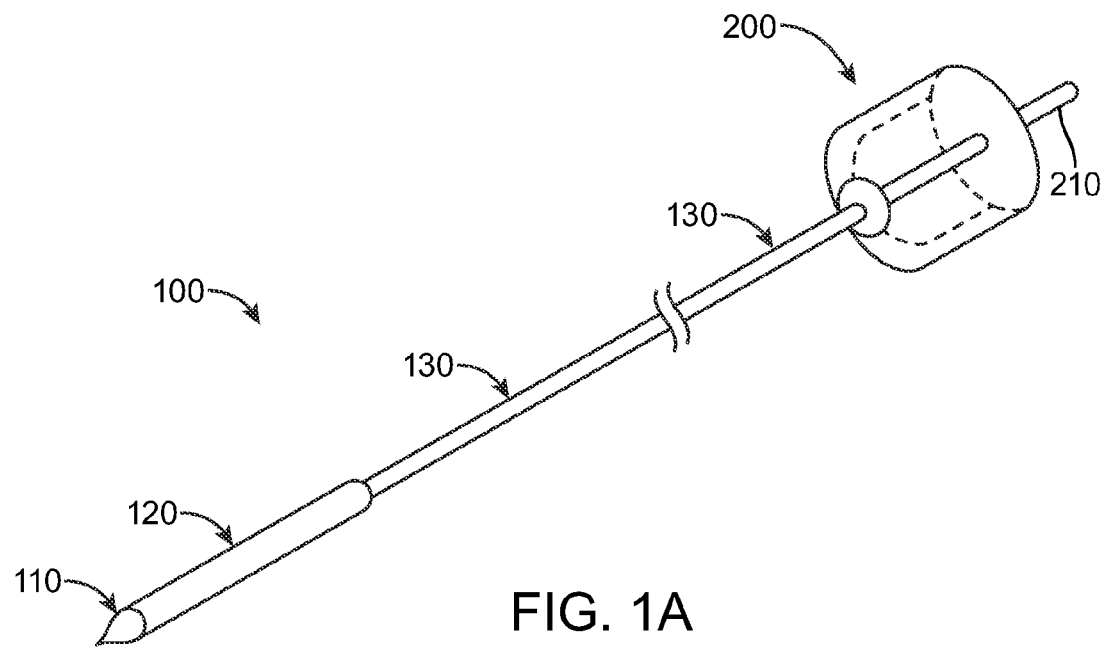
FIGS. 1A-1B illustrate an apparatus for actuating a delivery system in accordance with some embodiments.

While the disclosure refers to illustrative embodiments for particular embodiments, it should be understood that the disclosure is not limited thereto. Modifications can be made to the embodiments described herein without departing from the spirit and scope of the present disclosure. Those skilled in the art with access to this disclosure will recognize additional modifications, embodiments, and embodiments within the scope of this disclosure and additional fields, in which the disclosed examples could be applied. Therefore, the following detailed description is not meant to be limiting. Further, it is understood that the apparatus and methods described below can be implemented in many different embodiments of hardware. Any actual hardware described is not meant to be limiting. The operation and behavior of the apparatus and methods presented are described with the understanding that modifications and variations of the embodiments are possible.

References to "one embodiment," "an embodiment," "some embodiments," "in certain embodiments," etc. . . . , indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In some embodiments an electromechanical adapter or apparatus is disclosed. In some embodiments an adapter helps simplify the mechanical system associated with using an electromechanical system to load or deploy a prosthesis. This adapter may be configured to help control forces required for such loading and deploying of a prosthesis. In some embodiments this adapter is configured to apply an appropriate amount of force or torque such that a prosthesis can be loaded or deployed. The adapter may provide a convenient delivery device to be used as part of an electromechanical system. In some embodiments the adapter is configured to be used with other tools sometimes found in a hospital, operating room, or other area in which a patient is undergoing treatment.

In some embodiments, as shown in FIGS. 1-4, adapter 200 is configured to actuate a delivery system. In some embodiments adapter 200 is configured to actuate a catheter-based delivery system. In some embodiments adapter 200 comprises input shaft 210. In some embodiments adapter 200 comprises a first actuator 220 and a second actuator 230. In some embodiments adapter 200 comprises a stopper 240. In some embodiments adapter 200 comprises a torque limiter 250. In some embodiments adapter 200 comprises a gearbox 260. In some embodiments adapter 200 comprises an opening 270.

Figure 1B:
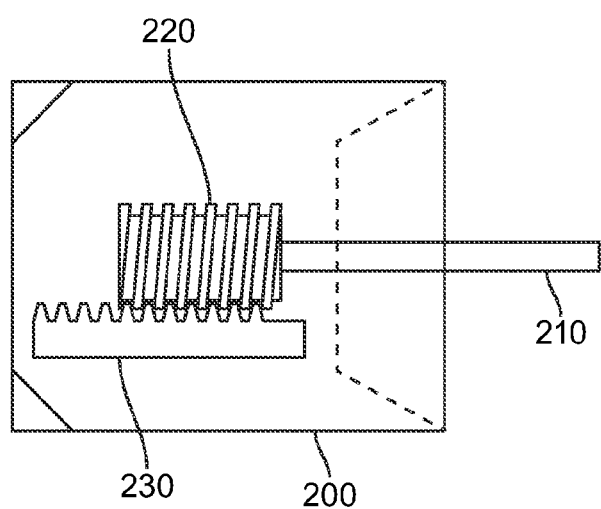

In some embodiments, as shown in FIG. 1B, adapter 200 comprises input shaft 210 and a first actuator 220. This first actuator 220 may be coupled to the input shaft 210. In some embodiments the adapter comprises a first actuator 220 and a second actuator 230. In some embodiments the second actuator 230 is configured to be coupled to a first catheter-based delivery system.

Figure 2:
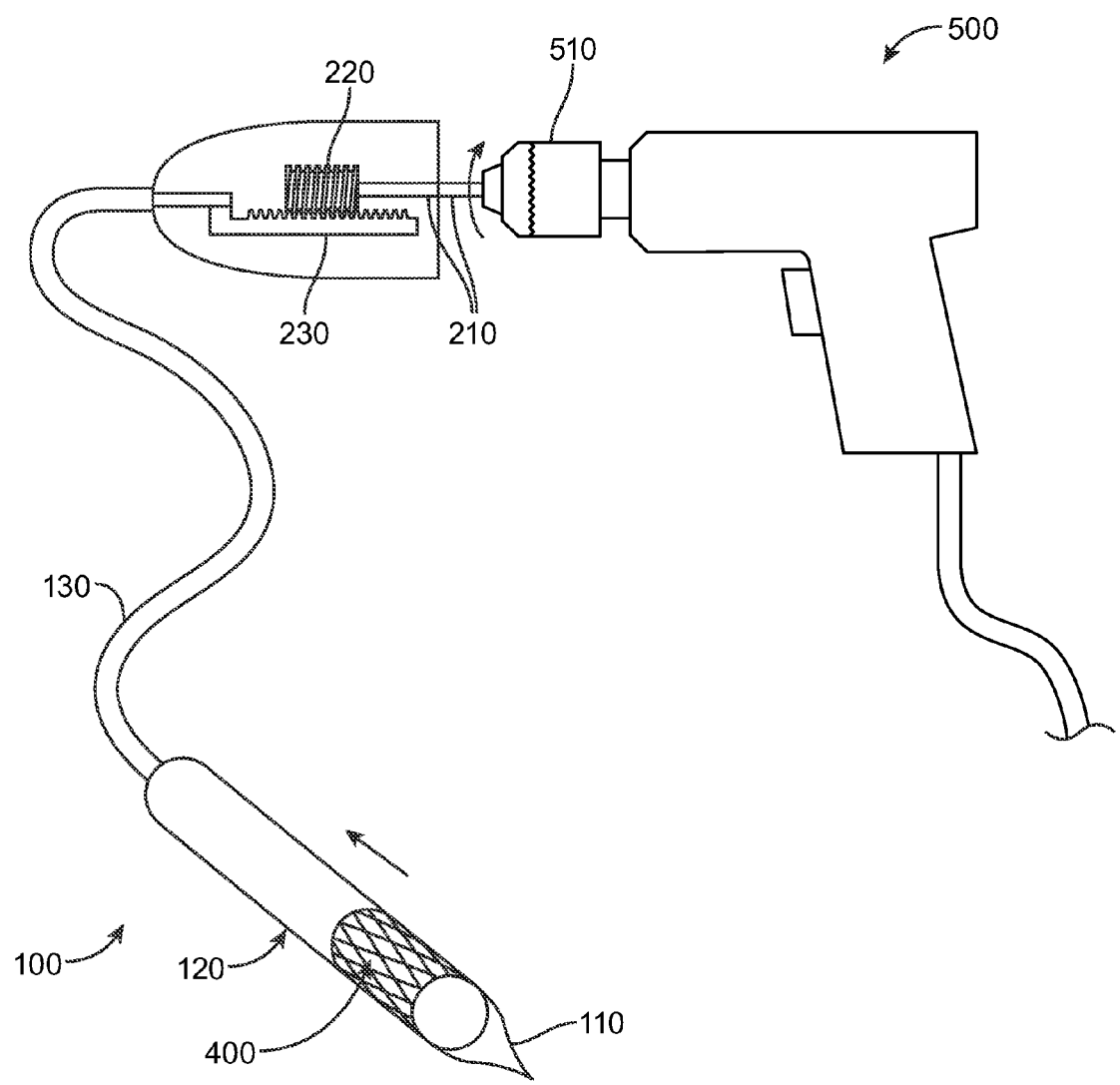
FIGS. 2-4 illustrate apparatus for actuating a delivery system in accordance with some embodiments.
Figure 3:
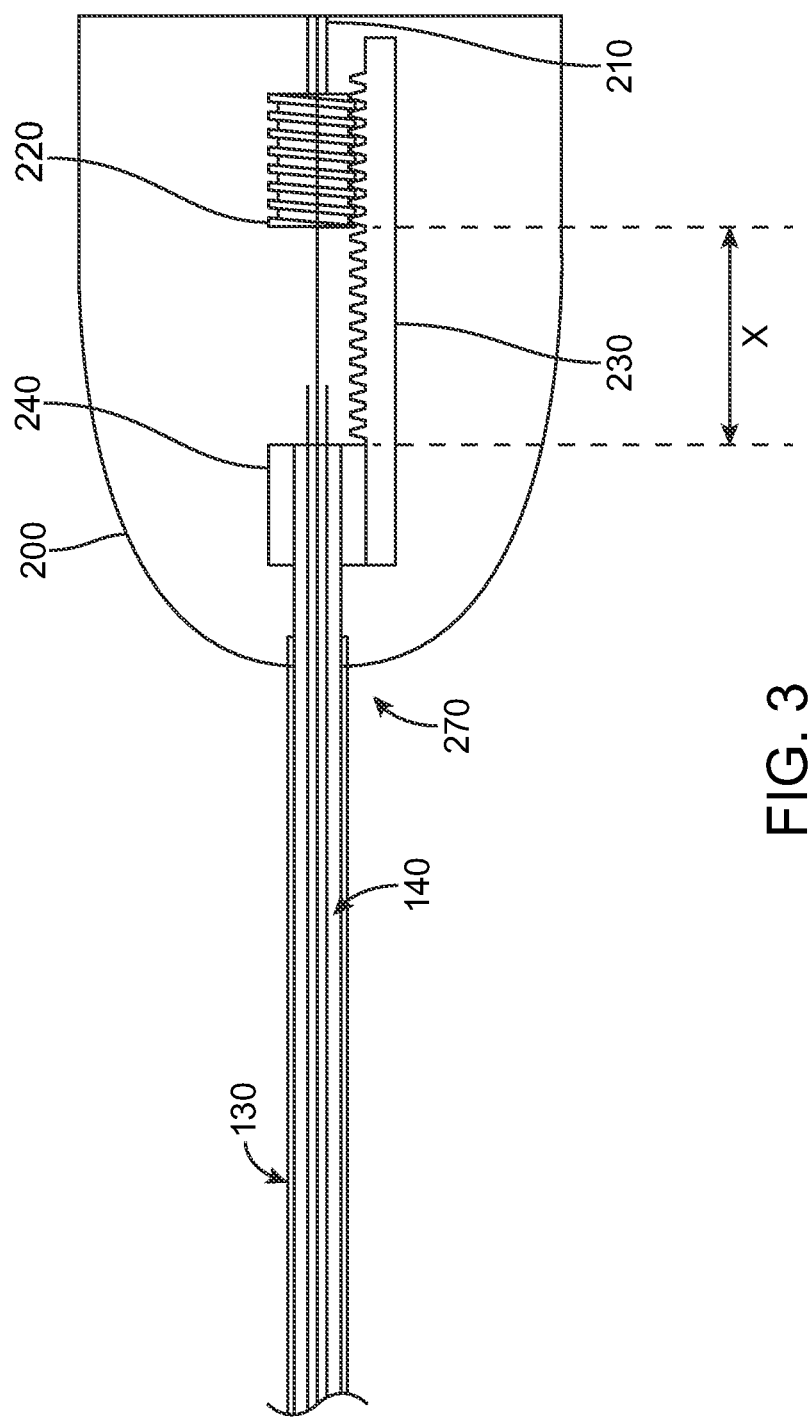

In some embodiments, as shown in FIGS. 1-3, a first catheter-based delivery system may comprise catheter 100. In some embodiments catheter 100 may comprise tip 110, capsule 120, outer sheath 130, and inner sheath 140. In some embodiments first actuator 220 is configured to actuate or drive second actuator 230. In some embodiments when first actuator 220 actuates second actuator 230 the adapter 200 is configured to actuate a portion of a delivery system. In some embodiments when first actuator 220 actuates second actuator 230 the adapter 200 is configured to actuate a portion of catheter 100. In some embodiments when first actuator 220 actuates second actuator 230, the adapter 200 is configured to actuate tip 110.

In some embodiments, as shown in FIG. 2, second actuator 230 is configured to move linearly after being actuated. In some embodiments second actuator 230 is configured for translational motion. In some embodiments first actuator 220 is configured to rotate. In some embodiments the rotational motion of first actuator 220 produces translational motion of second actuator 230. In some embodiments input shaft 210 of adapter 200 is configured to be coupled to an additional mechanism. The input shaft 210 may be configured to be actuated by a motor. The input shaft 210 may be configured to be actuated by a drill 500. The input shaft 210 may be configured to be actuated by a motorized drill 500.

In some embodiments, as shown in FIG. 3, the adapter 200 is configured to limit the amount of translational motion of second actuator 230 by a stopper 240. In some embodiments stopper 240 is a limit switch. In some embodiments stopper 240 prevents motion. In some embodiments stopper 240 limits motion.

In some embodiments adapter 200 is separate from a delivery system and a motorized device. In some embodiments adapter 200 is an isolated assembly or apparatus. In some embodiments adapter 200 is coupled to a delivery system. In some embodiments adapter 200 may be coupled to catheter 100. In some embodiments adapter 200 may be connected to catheter 100. In some embodiments adapter 200 comprises catheter 100.

In some embodiments, as shown in FIGS. 1-3, catheter 100 comprises a tip 110, a capsule 120, and an inner sheath 140. In some embodiments tip 110 is adjacent to capsule 120. In some embodiments capsule 120 is adjacent to inner sheath 140. In some embodiments adapter 200 comprises input shaft 210, first actuator 220, second actuator 230, and stopper 240. The second actuator 230 may be configured for translational motion. In some embodiments second actuator 230 is configured to provide translational motion to a portion of catheter 100. In some embodiments catheter 100 is configured to be translated or moved by another element of the system, such as second actuator 230. The translational motion of second actuator 230 may correspond to translational motion of tip 110.

Figure 4:
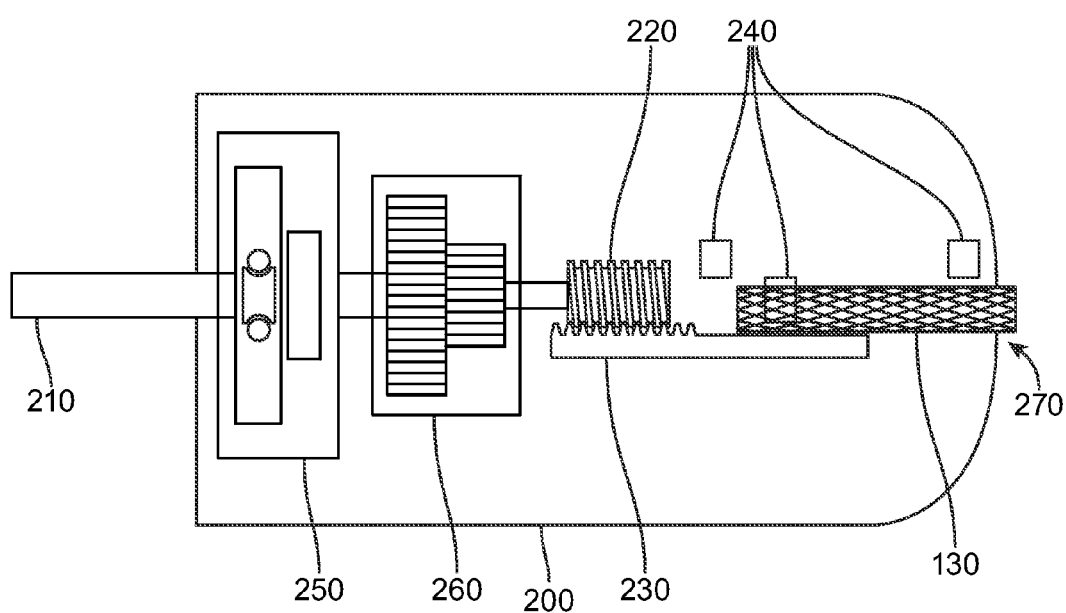

In some embodiments, as shown in FIG. 4, adapter 200 comprises a torque limiter 250. In some embodiments torque limiter 250 is configured to limit output torque of adapter 200. In some embodiments adapter 200 comprises a gearbox 260. In some embodiments gear box 260 is configured to transmit energy from one element of adapter 200 to another element of adapter 200. The gearbox 260 may be configured to increase the torque and reduce the speed of some elements of adapter 200. The gearbox 260 may decrease the torque and increase the speed of some elements of adapter 200. The gear box 260 may help change the operating speed of adapter 200 relative to the operating speed of input shaft 210.

Some embodiments disclose a method of actuating a delivery system using an electrically powered apparatus. In some embodiments this method includes attaching an apparatus to a delivery system. In some embodiments this method includes attaching adapter 200 to catheter 100. In some embodiments an electrically powered apparatus is attached to a catheter-based delivery system. In some embodiments a catheter-based delivery system comprises catheter 100. In some embodiments the apparatus comprises an adapter 200. In some embodiments adapter 200 comprises an input shaft 210 and a first actuator 220 attached to input shaft 210. In some embodiments first actuator 220 is configured to interact with a second actuator 230. In some embodiments second actuator 230 is coupled to a catheter-based delivery system. In some embodiments second actuator is coupled to catheter 100.

In some embodiments the method comprises actuating an input shaft 210 via a power source. In some embodiments the method comprises actuating the catheter-based delivery system via the adapter 200. In some embodiments the method comprises actuating the catheter 100 via the adapter 200.

In some embodiments a power source comprises a drill 500. In some embodiments a power source comprises a motorized drill 500. In some embodiments actuating a catheter 100 comprises advancing the catheter 100 via the first actuator 220 and second actuator 230 by the drill 500. In some embodiments advancing catheter 100 comprises imparting translational movement to catheter 100 via one or both of first actuator 220 and second actuator 230.

In some embodiments an apparatus comprises adapter 200. In some embodiments an apparatus comprises adapter 200 and catheter 100. In some embodiments adapter 200 comprises an input shaft 210, first actuator 220, and second actuator 230.

In some embodiments catheter 100 comprises tip 110, capsule 120, and inner sheath 140. In some embodiments tip 110 is adjacent capsule 120. In some embodiments capsule 120 is adjacent to inner sheath 140. In some embodiments adapter 200 is configured to receive inner sheath 140. In some embodiments adapter 200 is configured to receive inner sheath 140 via opening 270.

The catheter 100 may be configured to be coupled to adapter 200. The catheter 100 may be configured to be attached to adapter 200. The catheter 100 may also be configured to be joined to adapter 200. The catheter 100 may be configured to be connected to adapter 200.

In some embodiments catheter 100 may be configured to contain a medical device. The catheter 100 may be configured to contain a prosthetic heart valve 400. In some embodiments catheter 100 may be configured to have a medical device disposed on catheter 100. The catheter 100 may be configured to have a prosthetic heart valve 400 disposed on catheter 100. In some embodiments catheter 100 may be configured to have a medical device disposed in catheter 100. The catheter 100 may be configured to have a prosthetic heart valve 400 disposed in catheter 100.

In some embodiments capsule 120 may be configured to contain a prosthetic heart valve 400. In some embodiments capsule 120 may be configured to have a medical device disposed on capsule 120. In some embodiments capsule 120 may be configured to have a prosthetic heart valve 400 disposed on capsule 120.

In some embodiments adapter 200 is configured to actuate catheter 100. In some embodiments adapter 200 is configured to impart translational motion to catheter 100. In some embodiments adapter 200 is configured to produce translational motion of inner sheath 140. In some embodiments adapter 200 is configured to produce translational motion of outer sheath 130. In some embodiments adapter 200 is configured to produce translational motion of capsule 120. In some embodiments adapter 200 is configured to produce translational motion of tip 110.

Adapter 200 may be configured to impart translational motion to catheter 100 via a first actuator 220. In some embodiments adapter 200 is configured to impart translational motion to catheter 100 via a first actuator 220 and a second actuator 230. In some embodiments adapter 200 is configured to impart translational motion to catheter 100 via a second actuator 230. In some embodiments adapter 200 is configured to impart translational motion to a portion of catheter 100 or via a drill 500. In some embodiments adapter 200 is configured to impart translational motion to a portion of catheter 100 or via a surgical drill 500. In some embodiments adapter 200 is configured to impart translational motion to a portion of catheter 100 or via a drill 500 with a chuck mechanism.

Adapter 200 may comprise an input shaft 210. In some embodiments adapter 200 comprises first actuator 220. In some embodiments adapter 200 comprises second actuator 230. In some embodiments first actuator 220 may comprise a gear. In some embodiments first actuator 220 may comprise an actuator different from a gear. In some embodiments second actuator 230 may comprise a gear. In some embodiments second actuator 230 may comprise an actuator different from a gear.

In some embodiments first actuator and second actuator 230 are configured to contact one another. In some embodiments first actuator 220 may comprise a rotational gear. In some embodiments first actuator 220 may comprise a pinion gear. In some embodiments second actuator 230 may comprise a rack gear. In some embodiments the rotational motion of first actuator 220 may create rotate translational motion of second actuator 230. In some embodiments first actuator 220 is configured to be rotated clockwise or counterclockwise or both. In some embodiments second actuator 230 is configured to translate away from first actuator 220. In some embodiments second actuator 230 is configured to translate toward first actuator 220.

A motorized device 600 or drill 500 may be coupled to the input shaft 210. In some embodiments a motorized device 600 or drill 500 may be connected to the input shaft 210. In some embodiments a motorized device 600 or drill 500 may be joined to the input shaft 210.

In some embodiments second actuator 230 is configured to translate toward motorized device 600 or drill 500. In some embodiments second actuator 230 is configured to translate toward motorized device 600 or drill 500 when motorized device 600 or drill 500 is connected to input shaft 210. In some embodiments second actuator 230 is configured to translate toward motorized device 600 or drill 500. In some embodiments second actuator 230 is configured to translate away from motorized device 600 or drill 500 when motorized device 600 or drill 500 is connected to input shaft 210.

The first actuator 220 may be configured to be a worm gear. In some embodiments second actuator 230 is configured to be a worm gear. In some embodiments any actuator may comprise a gear, an auger, a lever, an arm, or any other suitable device known to a person of ordinary skill in the art.

Catheter 100 may include tip 110, capsule 120, inner sheath 140, and outer sheath 130. In some embodiments tip 110 may comprise varying cross-sections. In some embodiments tip 110 may taper to a point. In some embodiments tip 110 will increase in cross-sectional area. In some embodiments tip 110 may be a blunt tip. In some embodiments tip 110 may be adjacent to capsule 120. In some embodiments tip 110 made taper from a smaller cross-sectional area to a larger cross-sectional area directly adjacent capsule 120.

In some embodiments capsule 120 is configured to contain a prosthetic heart valve 400. In some embodiments capsule 120 is configured to have a prosthetic heart valve 400 disposed on capsule 120. In some embodiments prosthetic heart valve 400 may be longer than capsule 120. In some embodiments prosthetic heart valve 400 may be longer than capsule 120. In some embodiments inner sheath 140 may be longer than capsule 120. In some embodiments inner sheath 140 may be shorter than capsule 120. In some embodiments capsule 120 may be longer than tip 110. In some embodiments capsule 120 may be shorter than tip 110.

The inner sheath 140 may be fed directly into adapter 200. In some embodiments adapter 200 is configured to couple inner sheath 140 within adapter 200. In some embodiments adapter 200 is configured to hold inner sheath 140 in a fixed position. In some embodiments adapter 200 is configured to receive inner sheath 140. In some embodiments adapter 200 is configured to couple inner sheath 140 with an element of adapter 200. In some embodiments adapter 200 is configured to connect inner sheath 140 with an element of adapter 200. In some embodiments adapter 200 is configured to attach inner sheath 140 with an element of adapter 200. In some embodiments adapter 200 is configured to receive inner sheath 140 such that inner sheath 140 is connected to first actuator 220. In some embodiments adapter 200 is configured to receive inner sheath 140 such that inner sheath 140 is connected to second actuator 230.

In some embodiments outer sheath 130 may be fed directly into adapter 200. In some embodiments adapter 200 is configured to couple outer sheath 130 with adapter 200. In some embodiments adapter 200 is configured to hold outer sheath 130 in a fixed position. In some embodiments adapter 200 is configured to receive outer sheath 130. In some embodiments adapter 200 is configured to couple outer sheath 130 with an element of adapter 200. In some embodiments adapter 200 is configured to connect inner outer sheath 130 with an element of adapter 200. In some embodiments adapter 200 is configured to attach outer sheath 130 with an element of adapter 200. In some embodiments adapter 200 is configured to receive outer sheath 130 such that in outer sheath 130 is connected to first actuator 220. In some embodiments adapter 200 is configured to receive outer sheath 130 such that outer sheath 130 is connected to second actuator 230.

In some embodiments adapter 200 is configured to translate rotational motion of first actuator 220 into translational motion is second actuator 230. In some embodiments this translational motion may be linear motion. In some embodiments adapter 200 is configured to use stopper 240 to limit translational motion of second actuator 230. In some embodiments adapter 200 is configured to use stopper 240 to limit translational motion of catheter 100.

In some embodiments adapter 200 comprises multiple stoppers 240. In some embodiments a stopper 240 prevents translational motion or limits translational motion in one direction. In some embodiments a second stopper 240 limits translational motion in another direction.

In some embodiments actuator 200 may contain at least a portion of catheter 100. In some embodiments actuator 200 may encompass at least a portion of catheter 100. In some embodiments actuator 200 may cover at least a portion of catheter 100.

The actuator 200 may contain at least a portion of inner sheath 140. The actuator 200 may encompass at least a portion of inner sheath 140. The actuator 200 may cover at least a portion of inner sheath 140.

The actuator 200 may contain at least a portion of outer sheath 130. The actuator 200 may encompass at least a portion of outer sheath 130. The actuator 200 may cover at least a portion of outer sheath. The actuator 200 may contain at least a portion of input shaft 210. The actuator 200 may encompass at least a portion of 210. In some embodiments actuator 200 may cover at least a portion of 210.

The adapter 200 may comprise supports to hold portions of elements contained within adapter 200.

The adapter 200 may be configured to receive a protrusion extending from a motorized device 600. In some embodiments adapter 200 is configured to receive a protrusion extending from a drill 500. In some embodiments adapter 200 is configured to receive a protrusion extending from a chuck 510 of drill 500.

In some embodiments drill 500 may be a wireless device. In some embodiments drill 500 may be a battery operated device. In some embodiments drill 500 may be configured to plug into a power source. In some embodiments drill 500 may include a power source.

In some embodiments adapter 200 may comprise a torque limiter. In some embodiments torque limiter 250 will prevent drill 500 or motorized device 600 from over-torqueing the adapter 200 or a portion of the delivery system. In some embodiments torque limiter 250 will prevent over-torqueing when using drill 500 or motorized device 600 in conjunction with adapter 200.

The sterilizable power source may be used in conjunction with adapter 200. In some embodiments this sterilizable power source may be a drill 500. In some embodiments this sterilizable power source may be a motorized device 600. This prevents the need for physicians, hospitals, or other parties to replace power sources used during a procedure. This provides a cost-effective way to use an electromechanical system for procedures requiring a delivery system. This provides a cost-effective way to use an electromechanical system for procedures requiring a catheter 100.

In some embodiments catheter 100 includes an inner sheath 140 and an outer sheath 130. In some embodiments catheter 100 may only include one sheath. Descriptions of an inner sheath 140 or an outer sheath 130 should not be understood to be limiting. Any reference to an inner sheath 140 may be taken as a reference to outer sheath 130 unless contradictory. Any reference to an outer sheath 130 may be taken as a reference to inner sheath 140 unless contradictory.

As illustrated in FIG. 3, adapter 200 may comprise an input shaft 210, a first actuator 220, and a second actuator 230. In some embodiments adapter 200 may comprise a stopper 240. In some embodiments adapter 200 may include opening 270. In some embodiments opening 270 is configured to receive at least one sheath of catheter 100. In some embodiments opening 270 is configured to receive inner sheath 140. In some embodiments opening 270 is configured to receive outer sheath 130. In some embodiments opening 270 is configured to receive outer sheath 130 and inner sheath 140.

In some embodiments adapter 200 is configured to be coupled to inner sheath 140. In some embodiments adapter 200 is configured to be coupled to outer sheath 130. In some embodiments adapter 200 is configured to hold catheter 100 in place. In some embodiments a stopper 240 is attached to a second actuator 230. In some embodiments stopper 240 is configured to be coupled to second actuator 230. In some embodiments stopper 240 is stationary. In some embodiments stopper 240 is immovable. In some embodiments stopper 240 is configured to move. Stopper 240 may be configured to be stationary to limit the translational movement of some element or elements of adapter 200. This stopper 240 may prevent movement in any direction. For example, stopper 240 may limit or prevent the translational motion of second actuator 230. Stopper 240 may also be configured to move. Stopper 240 may be configured to move if a certain amount of force is applied. Stopper 240 may also be adjustable, such that for different operations of adapter 200, stopper 240 may be moved to provide different limits on the motion of the elements of adapter 200.

The stopper 240 may be configured to limit or prevent movement of first actuator 220. In some embodiments stopper 240 is configured to limit or prevent movement of second actuator 230. In some embodiments adapter 200 may be comprised of multiple embodiments. In some embodiments inner sheath 140 is configured to be disposed partially in adapter 200. In some embodiments outer sheath 130 is configured to be disposed partially in adapter 200.

In some embodiments adapter 200 is configured to receive one or both of inner sheath 140 and outer sheath 130. In some embodiments one of inner sheath 140 and outer sheath 130 can be contained in adapter 200. As illustrated in FIG. 3, inner sheath 140 is configured to be advanced farther into adapter 200 than outer sheath 130. In some embodiments first actuator 220 may comprise a gear. In some embodiments first actuator 220 may comprise an auger. In some embodiments first actuator 220 may comprise an actuator other than a gear.

The first actuator 220 may be configured to rotate clockwise. In some embodiments first actuator 220 may be configured to rotate counterclockwise. In some embodiments second actuator 230 may be configured to rotate. In some embodiments second actuator 230 may be configured for translation motion. This translation motion may be linear motion. In some embodiments second actuator 230 may be configured to translate a distance X. In some embodiments second actuator 230 is configured to travel a distance X where the distance X comprises a distance from one edge of a first actuator 222 to one edge of a stopper 240. In some embodiments second actuator 230 is configured to travel a distance different from distance X. In some embodiments the distance X may comprise a distance greater than the length of first actuator 220. In some embodiments the distance X may comprise a distance shorter than the length of first actuator 220. In some embodiments the distance or length X may be greater than the length of stopper 240. In some embodiments the distance or length X may be less than the length of stopper 240.

The first actuator 220 may be configured to be actuated by motorized device 600. In some embodiments first actuator 220 is configured to be actuated by drill 500. In some embodiments first actuator 220 is configured to be rotated by motorized device 600. In some embodiments first actuator 220 is configured to be rotated by drill 500. In some embodiments adapter 200 is configured to cover or enclose first actuator 220, second actuator 230, and stopper 240. In some embodiments adapter 200 is configured to contain first actuator 220, second actuator 230, and stopper 240.

In some embodiments adapter 200 is configured to at least partially contain catheter 100. In some embodiments adapter 200 is configured to at least partially contain inner sheath 140. In some embodiments adapter 200 is configured to at least partially contain outer sheath 130.

In some embodiments adapter 200 is configured to taper from a general cylinder shape to opening 270. In some embodiments a portion of adapter 200 housing comprises an arc. In some embodiments a portion of adapter 200 housing comprises a substantially straight section.

The width of adapter 200 may be greater than the width of catheter 100. In some embodiments the diameter of adapter 200 is greater than the diameter of catheter 100. In some embodiments the circumference of adapter 200 is greater than the circumference of catheter 100. In some embodiments the perimeter of adapter 200 is greater than the width of catheter 100.

Adapter 200 may comprise a rectangular shape. In some embodiments adapter 200 may comprise a square shape. In some embodiments adapter 200 may comprise a circular shape. In other embodiments adapter 200 may comprise another shape.

In some embodiments adapter 200 may comprise indentations on its exterior. In some embodiments adapter 200 may comprise a grip portion on its exterior.

In some embodiments adapter 200 may comprise an input shaft 210, a torque limiter 250, a gearbox 260, a first actuator 220, a second actuator 230, or a stopper 240. In some embodiments input shaft 210 extends out from adapter to 200. In some embodiments input shaft 210 is configured to be received by a drill 500. In some embodiments input shaft 210 is configured to be received by a motorized device 600.

In some embodiments input shaft 210 may have two ends. In some embodiments a first end of input shaft 210 is configured to be received by a drill 500 or a motorized device 600. In some embodiments a second end of input shaft 210 is configured to be attached to a first actuator 220. In some embodiments a second end of input shaft 210 is configured to be attached to a second actuator 230.

The input shaft 210 may comprise a first actuator 220 disposed on one end. In some embodiments gearbox 260 is disposed on input shaft 210. In some embodiments gearbox 260 is adjacent to first actuator 220. In some embodiments gearbox 260 is proximate to first actuator 220. In some embodiments input shaft 210 has multiple elements disposed on the shaft. In some embodiments first actuator 220, gearbox 260, and torque limiter 250 are all disposed on input shaft 210. In some embodiments first actuator 220 may be adjacent to gearbox 260. In some embodiments gearbox 260 may be adjacent torque limiter 250. In some embodiments torque limiter 250 may be adjacent to a portion of input shaft 210 configured to be received by drill 500 or motorized device 600. In some embodiments torque limiter 250 is configured to be adjacent to first actuator 220. In some embodiments gearbox 260 is configured to be adjacent to a portion of input shaft 210 configured to be received by a drill 500 or motorized device 600.

In some embodiments drill 500 is configured to rotate in a variable manner. In some embodiments gearbox 260 may prevent over-rotation of elements of adapter 200. In some embodiments gearbox 260 may prevent over-rotation of first actuator 220.

In some embodiments torque limiter 250 will prevent damage to elements of adapter 200. In some embodiments torque limiter 250 will prevent damage first actuator 220. In some embodiments torque limiter 250 will prevent damage to second actuator 230.

In some embodiments torque limiter 250 may be of any type. In some embodiments torque limiter 250 may be a shear pin type, a synchronous magnetic type, a ball detent type, a pawl and spring type, a friction plate type, a magnetic particle type, or a magnetic hysteresis type, or any other type.

The gearbox 260 may be any type of gearbox.

Adapter 200 may be configured to be used with multiple catheters 100. Adapter 200 may be configured to be used with multiple types of prosthetic heart valves 400. In some embodiments prosthetic heart valve 400 is a transcatheter heart valve. In some embodiments prosthetic heart valve 400 is a self-expandable heart valve. In some embodiments prosthetic heart valve 400 is a balloon-expandable heart valve. In some embodiments prosthetic heart valve 400 is a mechanically-expandable heart valve.

In some embodiments adapter 200 is configured to produce translational motion. In some embodiments adapter 200 is configured to rotate first actuator 220 at a variable speed. In some embodiments adapter 200 can be configured to rotate faster or slower as needed to move second actuator 230. In some embodiments adapter 200 can be configured to rotate faster or slower as needed to move catheter 100.

For example, in some embodiments adapter 200 may be configured to rotate at one speed for deployment of an aortic prosthetic heart valve 400. In some embodiments adapter 200 may be configured to rotate at one speed for deployment of a mitral prosthetic heart valve 400.

The adapter 200 may comprise mechanical or electrical limit switches. In some embodiments stoppers 240 may comprise mechanical limit switches. In some embodiments stoppers 240 may comprise electrical limit switches. In some embodiments other elements of adapter 200 may comprise mechanical or electrical limit switches.

The second actuator 230 may comprises a rack gear. In some embodiments second actuator 230 is threaded along a portion of its length. In some embodiments second actuator 230 is threaded along its entire length.

In some embodiments second actuator 230 is attached to catheter 100. In some embodiments second actuator 230 is attached to outer sheath 130. In some embodiments second actuator 230 is attached to inner sheath 140. In some embodiments second actuator 230 is coupled to catheter 100. In some embodiments second actuator 230 is coupled to outer sheath 130. In some embodiments second actuator 230 is coupled to inner sheath 140. In some embodiments second actuator 230 is joined to catheter 100. In some embodiments second actuator 230 is joined to outer sheath 130. In some embodiments second actuator 230 is joined to inner sheath 140.

In some embodiments adapter 200 comprises one stopper 240. In some embodiments adapter 200 comprises multiple stoppers 240. In some embodiments one stopper 240 is positioned near opening 270 of adapter 200. In some embodiments opening 270 is an opening proximate to where catheter 100 is received by adapter 200. In some embodiments stopper 240 is coupled to the wall of adapter 200. In some embodiments stopper 240 is connected to the wall of adapter 200.

In some embodiments a stopper 240 is configured to prevent second actuator 230 from moving toward drill 500. In some embodiments a stopper 240 is configured to prevent second actuator 230 from translational motion away from drill 500. In some embodiments stopper 240 is configured to be attached to a second actuator 230. In some embodiments adapter 200 comprises multiple stoppers 240.

The second actuator 230 may be attached to some portion of catheter 100 via adhesive. Or the second actuator 230 may be attached to some portion of catheter 100 via a clip. The second actuator 230 may be attached to some portion of catheter 100 via a loop. In some embodiments second actuator 230 may be attached to some portion of catheter 100 via a hook. In some embodiments second actuator 230 may be attached to some portion of catheter 100 via a detent. In some embodiments second actuator 230 may be attached to some portion of catheter 100 via a clamp. In some embodiments second actuator 230 may be attached to some portion of catheter 100 via a mechanical attachment means. In some embodiments second actuator 230 may be attached to some portion of catheter 100 via an electrical attachment means. In some embodiments stopper 240 may be configured to attach some portion of catheter 102 second actuator 230. In some embodiments stopper 240 may be attached to second actuator 230 via a mechanical method. In some embodiments stopper 240 may be attached to second actuator 230 via a mechanism.

In some embodiments catheter 100 may be attached to adapter 200. In some embodiments some or all of the elements of adapter 200 can be contained or housed in an adapter. Any number of elements may be contained within, be disposed on, or be surrounded by adapter 200 or some portion thereof.

In some embodiments some portion of adapter 200 may allow for visual verification or sight of at least one element contained within or partially contained within adapter 200. In some embodiments adapter 200 may have a designated window to examine elements or an element of adapter 200.

In some embodiments, as shown in FIGS. 6A-C, adapter 300 comprises input shaft 310, first actuator 320, second actuator 330, or third actuator 340. In some embodiments adapter 300 comprises a torque limiter 350. In some embodiments adapter 300 comprises a first output shaft 360. In some embodiments adapter 300 comprises a second output shaft 370. In some embodiments second actuator 330 comprises actuator shaft 332, rack gear 334, and pinion gear 336. In some embodiments third actuator 340 comprises actuator shaft 342, rack gear 344, and pinion gear 346.

Figure 5A:
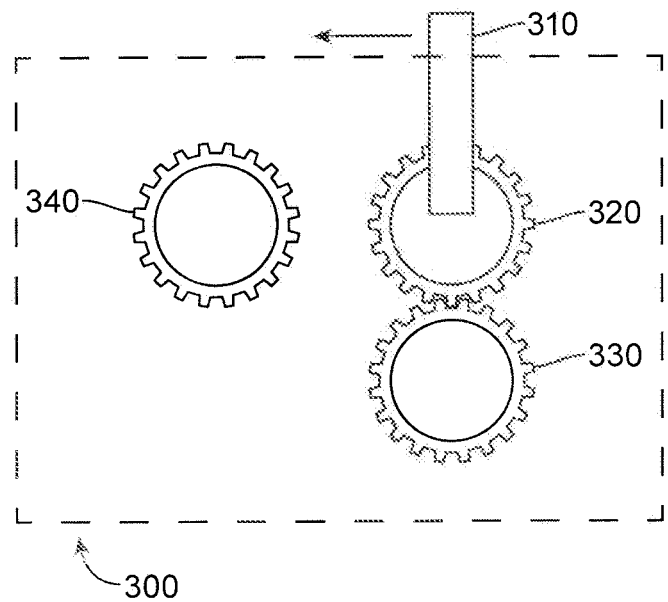
FIGS. 5A-5B illustrate an apparatus for actuating a delivery system in accordance with some embodiments.
Figure 5B:
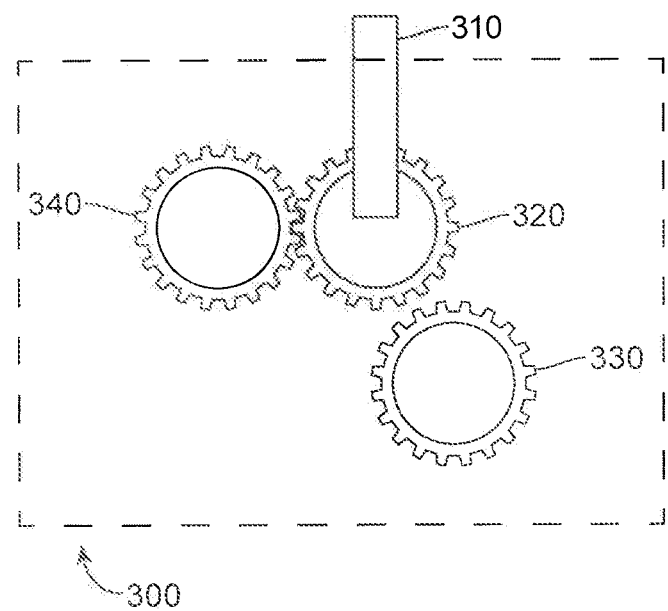
Figure 6:
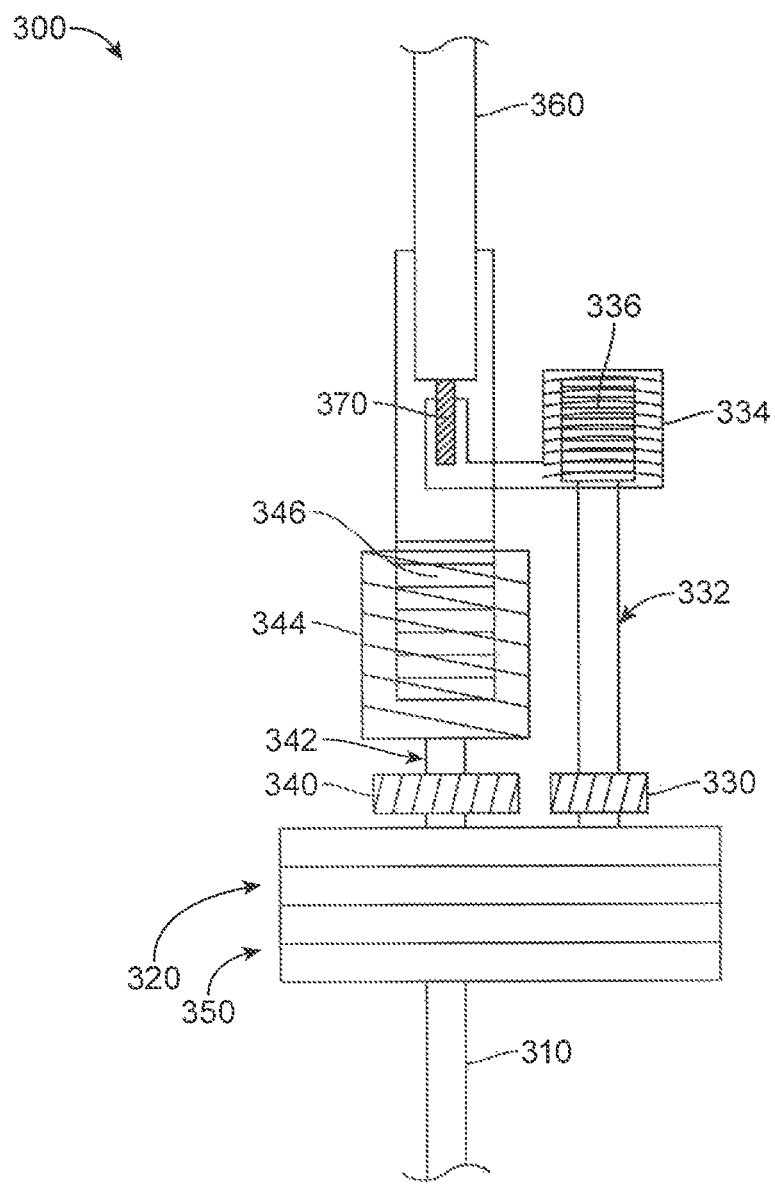
FIG. 6 illustrates an apparatus for actuating a delivery system in accordance with some embodiments.

In some embodiments, as shown in FIGS. 5A, 5B, and 6, adapter 300 comprises input shaft 310, first actuator 320, second actuator 330, or third actuator 340. In some embodiments adapter 300 comprises a torque limiter 350. In some embodiments adapter 300 comprises a first output shaft 360. In some embodiments adapter 300 comprises a second output shaft 370. In some embodiments second actuator 330 comprises actuator shaft 332, rack gear 334, and pinion gear 336. In some embodiments third actuator 340 comprises actuator shaft 342, rack gear 344, and pinion gear 346.

In some embodiments adapter 300 is configured such that first actuator 320 is configured to actuate third actuator 340. In some embodiments adapter 300 is configured such that first actuator 320 is configured to actuate second actuator 330. In some embodiments first actuator 320 is configured to actuate second actuator 330 and third actuator 340. In some embodiments first actuator 320 is configured to actuate second actuator 330 and third actuator 340 simultaneously.

In some embodiments an input shaft 310 of adapter 300 determines which actuator the first actuator 320 will actuate. In some embodiments input shaft 310 functions as a selector lever. In some embodiments when input shaft 310 is in a first position, first actuator 320 will actuate second actuator 330. In some embodiments when input shaft 310 is in a second position, first actuator 320 will actuate third actuator 340. In some embodiments adapter 300 may have multiple actuators. In some embodiments first actuator 320 may be configured to actuate three or more actuators. In some embodiments first actuator 320 may be configured to actuate multiple actuators at the same time.

In some embodiments adapter 300 comprises an input shaft 310 and a first actuator 320. In some embodiments adapter 300 comprises a second actuator 330. In some embodiments adapter 300 comprises a third actuator 340. In some embodiments adapter 300 comprises a torque limiter 350. In some embodiments adapter 300 comprises a first output shaft 360. In some embodiments adapter 300 comprises a second output shaft 370.

In some embodiments adapter 300 is configured to actuate multiple catheters 100. In some embodiments a first actuator 320 of adapter 300 can be configured to actuate a second actuator 330 corresponding to portion of a first catheter 100 system. In some embodiments a first actuator 320 of adapter 300 can be configured to actuate a third actuator 340 corresponding to a second catheter 100 system. In some embodiments a first actuator 320 of adapter 300 can be configured to actuate a third actuator 340 corresponding to a second portion of a first catheter 100 system.

In some embodiments the first actuator 320 may be configured to actuate one of second actuator 330 or third actuator 340. In some embodiments first actuator 320 may be configured to actuate second actuator 330 and its corresponding first catheter 100 system as well as third actuator 340 and its corresponding second catheter 100 system. In some embodiments first actuator 320 may be configured to actuate second actuator 330 and its corresponding first portion of a first catheter 100 system as well as third actuator 340 and its corresponding second portion of a first catheter 100 system.

In some embodiments second actuator 330 may be coupled to the actuator shaft 332. In some embodiments second actuator 330 may be coupled to actuator shaft 332 and a pinion gear 336. In some embodiments the pinion gear 336 may contact the rack gear 334. In some embodiments the rack gear 334 may move when pinion gear 336 is rotated by actuator shaft 332 as a result of second actuator 330 being actuated. In some embodiments the translational motion of rack gear 334 determines the translational motion of second output shaft 370. In some embodiments second output shaft 370 is coupled to catheter 100. In some embodiments second output shaft 370 is coupled to inner sheath 140 of catheter 100. In some embodiments second output shaft 370 is coupled to outer sheath 130 of catheter 100.

In some embodiments third actuator 340 may be coupled to the actuator shaft 342. In some embodiments third actuator 340 may be coupled to actuator shaft 342 and a pinion gear 346. In some embodiments the pinion gear 346 may contact the rack gear 344. In some embodiments the rack gear 344 may move when pinion gear 346 is rotated by actuator shaft 342 as a result of third actuator 340 being actuated. In some embodiments the translational motion of rack gear 344 determines the translational motion of first output shaft 360. In some embodiments first output shaft 360 is coupled to catheter 100. In some embodiments first output shaft 360 is coupled to inner sheath 140 of catheter 100. In some embodiments second output shaft 370 is coupled to outer sheath 130 of catheter 100.

In some embodiments second output shaft 370 may be concentric to first output shaft 360, as shown in FIG. 6A. In some embodiments second output shaft 370 may be adjacent to first output shaft 360. In some embodiments second output shaft 370 may be proximate to first output shaft 360. In some embodiments adapter 300 may comprise a torque limiter 350.

In some embodiments second output shaft 370 may be concentric to first output shaft 360, as shown in FIG. 6. In some embodiments second output shaft 370 may be adjacent to first output shaft 360. In some embodiments second output shaft 370 may be proximate to first output shaft 36a. In some embodiments adapter 300 may comprise a torque limiter 350.

In some embodiments some or all of the elements of adapter 300 can be contained or housed in an adapter. Any number of elements may be contained within, be disposed on, or be surrounded by adapter 300 or some portion thereof.

In some embodiments some portion of adapter 300 may allow for visual verification or sight of at least one element contained within or partially contained within adapter 300. In some embodiments adapter 300 may have a designated window to examine elements or an element of adapter 300.

In some embodiments first actuator 320 comprises a gear. In some embodiments first actuator 320 may provide a link to other actuators. In some embodiments input shaft 310 actuates first actuator 320. In some embodiments first actuator 320 actuates a second actuator 330. In some embodiments first actuator 320 actuates a third actuator 340.

In some embodiments adapter 300 is configured to have a movable first actuator 320. In some embodiments first actuator 320 is configured to contact or align with second actuator 330. In some embodiments first actuator 320 is configured to contact or align with third actuator 340. In some embodiments first actuator 320 is coupled to the input shaft 310. In some embodiments input shaft 310 and first actuator 320 are configured to move such that first actuator 320 will contact second actuator 330. In some embodiments input shaft 310 and first actuator 320 are configured to move such that first actuator 320 will contact third actuator 340.

In some embodiments input shaft 310 will actuate first actuator 320 which will then actuate second actuator 330. In some embodiments input shaft 310 will actuate first actuator 320 which will then actuate third actuator 340. In some embodiments moving the first actuator can be performed via a selector lever. In some embodiments the input shaft 310 may be a selector lever. In some embodiments the selector lever may be a separate element.

In some embodiments adapter 300 may be configured to permit movement of first actuator 320 via a mechanical lever. In some embodiments adapter 300 may be configured to permit movement of first actuator 320 via an electrical actuator. In some embodiments the first actuator 320 is configured to be moved manually. In some embodiments the first actuator 320 is configured to be moved automatically.

Figure 8A:
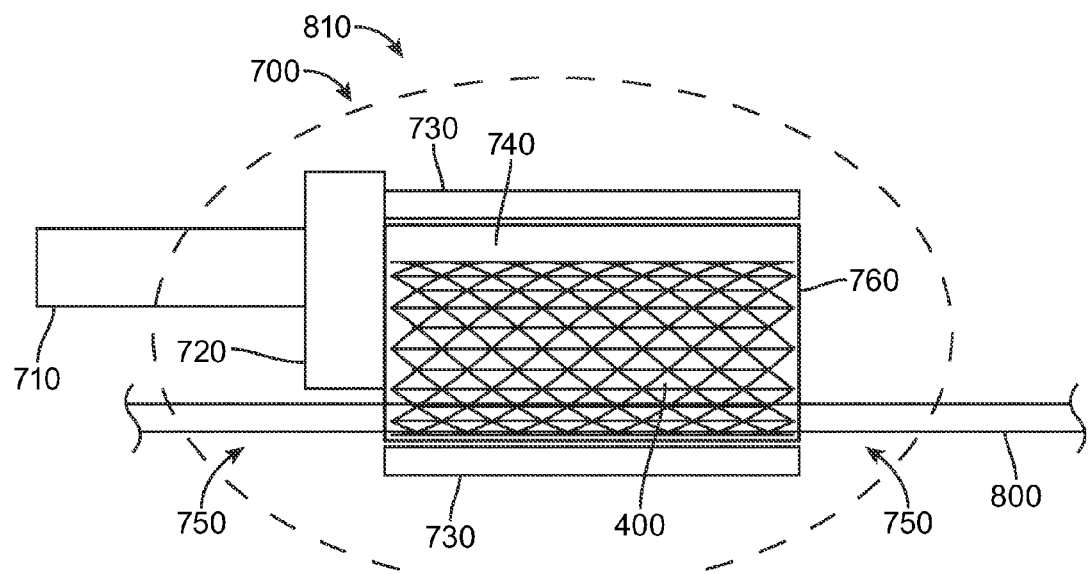
FIGS. 8A and 8B illustrate an apparatus for actuating a delivery system in accordance with some embodiments.
Figure 8B:
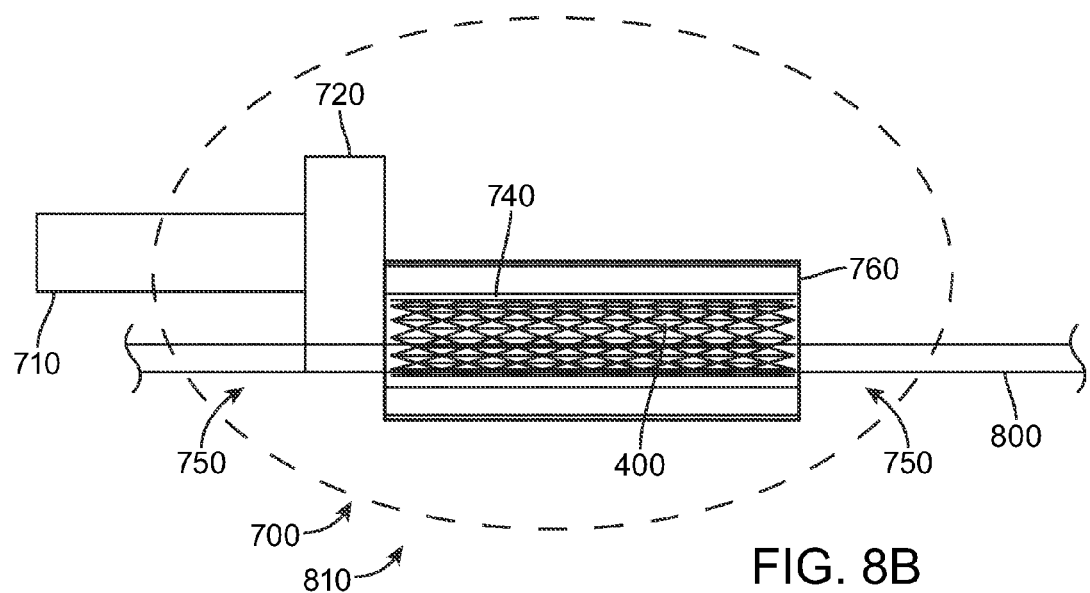

In some embodiments, as shown in FIGS. 7-8, adapter 700 is configured to compress or crimp an article. In some embodiments adapter 700 comprises an input shaft 710, a first actuator 720, a compressor 730, or a compression chamber 740. In some embodiments adapter 700 comprises lumen 750. In some embodiments adapter 700 comprises door 760. In some embodiments adapter 700 may not comprise door 760 but may instead only have an opening.

In some embodiments adapter 700 comprises an input shaft 710, a first actuator 720, a compressor 730, and a compression chamber 740. In some embodiments first actuator 720 is configured to be actuated by a motor. In some embodiments a motor comprises a motorized device 600. In some embodiments a motor comprises a drill 500. In some embodiments compression chamber 740 is a channel. In some embodiments compression chamber 740 is a slot. In some embodiments compression chamber 740 is configured to receive a prosthetic heart valve 400. In some embodiments compression chamber 740 is configured to receive an article.

In some embodiments compression chamber 740 is configured to compress or crimp a portion of a prosthetic heart valve 400 via the compressor 730. The compressor 730 may be a second actuator of adapter 700. The compressor 730 may comprise a spring. In some embodiments compressor 730 comprises an arm. The compressor 730 may comprise a lever. In some embodiments compressor 730 comprises multiple arms. In some embodiments compressor 730 comprises multiple springs. In some embodiments prosthetic heart valve 400 is a transcatheter heart valve. In some embodiments prosthetic heart valve 400 is a self-expandable heart valve. In some embodiments prosthetic heart valve 400 is a balloon-expandable heart valve. In some embodiments prosthetic heart valve 400 is a mechanically-expandable heart valve.

The compression chamber 740 may be configured to receive elements of a prosthetic heart valve 400. In some embodiments compression chamber 740 is configured to receive a valve assembly. The compression chamber 740 may be configured to receive a valve frame. In some embodiments compression chamber 740 is configured to couple, join, or attach a valve assembly to a valve frame together.

In some embodiments adapter 700 comprises a detachable portion. In some embodiments a detachable portion includes a handle. In some embodiments compression chamber 740 is configured to compress an article into a shape. For example compression chamber 740 may be configured to compress an article into a cylinder.

In some embodiments compression chamber is configured to compress an article via the compressor 730. In some embodiments compression chamber 740 is configured to compress an article via a second actuator. In some embodiments the compressed article is configured to be disposed on a catheter 100 after being compressed. In some embodiments the compressed article is disposed on a catheter 100 after being compressed.

Adapter 700 may be configured to compress a portion of an article. In some embodiments adapter 700 is configured to compress a prosthetic heart valve 400. In some embodiments the article may comprise a heart valve. The adapter 700 may comprise an input shaft 710. The adapter 700 may comprise a first actuator 720. In some embodiments adapter 700 may comprise a compressor 730. In some embodiments compressor 730 may be an actuator. In some embodiments adapter 700 may comprise a compression chamber 740. In some embodiments adapter 700 may comprise a lumen 750. In some embodiments adapter 700 may comprise a door 760.

In some embodiments input shaft 710 is configured to rotate. In some embodiments input shaft 710 is configured to be rotated via a drill 500. In some embodiments input shaft 710 is configured to be rotated via a motorized device 600. In some embodiments input shaft 710 actuates a first actuator 720. In some embodiments a first actuator 720 actuates compressor 730. In some embodiments a first actuator 720 actuates compressors 730. In some embodiments compressor 730 at least partially compresses a portion of an article or a prosthetic heart valve 400. In some embodiments compressor 730 is configured to compress multiple portions of an article or prosthetic heart valve 400.

In some embodiments compressor 730 is configured to collapse prosthetic heart valve 400 to a collapsed state. In some embodiments compression chamber 740 is configured to receive an article. In some embodiments compression chamber 740 is configured to receive a prosthetic heart valve 400.

In some embodiments compressor 730 comprises a spring. In some embodiments compressor 730 comprises multiple springs. In some embodiments compressor 730 comprises multiple springs of varying strength. In some embodiments compressor 730 is rotated such that at least a portion of a prosthetic heart valve 400 is compressed. In some embodiments, as shown in FIGS. 7-8, adapter 700 is configured to receive a catheter assembly 800. In some embodiments adapter 700 is configured to receive catheter 100. In some embodiments catheter assembly 800 comprises a handle 810.

In some embodiments adapter 700 is configured to receive catheter assembly 800. In some embodiments adapter 700 is configured such that catheter assembly 800 can pass through adapter 700. In some embodiments adapter 700 is configured such that catheter 100 can pass through adapter 700. In some embodiments adapter 700 is configured to compress a prosthetic heart valve 400 such that the prosthetic heart valve is disposed on a catheter 100 or catheter assembly 800 after it is compressed or crimped. In some embodiments catheter assembly 800 is configured to detach from adapter 700. In some embodiments catheter assembly 800 is configured to attach to adapter 700. In some embodiments catheter assembly 800 is configured to releasably attach to adapter 700.

In some embodiments adapter 700 is modular. In some embodiments adapter 700 includes catheter assembly 800. In some embodiments adapter 700 is modular such that certain elements may be detached from or attached to adapter 700. In some embodiments adapter 700 includes catheter 100. In some embodiment adapter 700 is modular such that certain elements may be detached from or attached to adapter 700.

The adapter 700 may comprise a door 760. In some embodiments door 760 may open such that prosthetic heart valve 400 may be loaded into compression chamber 740 through door 760. In some embodiments compressor 730 may comprise an arm. In some embodiments compressor 730 may comprise arms. In some embodiments compressor 730 may compress at least a portion of a prosthetic heart valve 400 loaded into compression chamber 740. In some embodiments compressors 730 may compress multiple portions of prosthetic heart valve 400. In some embodiments prosthetic heart valve 400 may be compressed into a cylinder. In some embodiments first actuator 720 is configured to actuate compressor 730 or compressors 730 such that an article or a prosthetic heart valve 400 is at least partially compressed.

The adapter 700 may be contained in a portion of a catheter assembly 800. In some embodiments the adapter 700 is contained in a portion of a handle 810. In some embodiments adapter 700 is configured such that a portion of catheter assembly 800 can pass through adapter 700. In some embodiments the catheter assembly 800 may be present in adapter 700 while the compressor 730 compresses a portion of a prosthetic heart valve 400. In some embodiments a prosthetic heart valve 400 may be disposed on a catheter assembly 800 after compressor 730 compresses a portion of prosthetic heart valve 400.

In some embodiments a motorized device 600 may comprise a modular motor section. In some embodiments a motorized device 600 may comprise a detachable modular motor section. In some embodiments a motorized device 600 may comprise a modular motor section that can be attached to a section of handle 810. In some embodiments a motorized device 600 may comprise a reusable modular motor section.

The adapter 700 may be configured to permit advancing prosthetic heart valve 400 out of adapter 700, while the adapter 700 is at least partially compressed. In some embodiments adapter 700 is configured to permit advancing prosthetic heart valve 400 via a portion of catheter assembly 800. In some embodiments adapter 700 is configured to permit advancing prosthetic heart valve 400 via a portion of catheter 100.

In some embodiments the door 760 may be configured to compress a portion of a prosthetic heart valve 400 disposed inside the compression chamber 730. In some embodiments adapter 700 may be configured such that such that when the door 760 is closed a portion of prosthetic heart valve 400 is compressed. In some embodiments the door 760 may be configured to compress the entire prosthetic heart valve 400 disposed inside the compression chamber 730. In some embodiments adapter 700 may be configured such that such that when the door 760 is closed the entire prosthetic heart valve 400 is compressed.

The foregoing description has been presented for purposes of illustration and description. Any structure, elements, or portions described can be contained in or part of a single or multiple structures. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. An apparatus for actuating a delivery system, the apparatus comprising:
   an input shaft having a proximal portion and a distal portion, the proximal portion of the input shaft configured to be rotated by a motorized device;
   a first actuator coupled to the distal portion of the input shaft, wherein the first actuator is configured to rotate upon rotation of the input shaft;
   a second actuator coupled to the first actuator and configured to be coupled to a first catheter-based delivery system such that the first catheter-based delivery system is distal of the distal portion of the input shaft,
   wherein the first actuator is configured to actuate the second actuator such that a rotation of the first actuator causes a translational motion of the second actuator, and wherein the translational motion of the second actuator is configured to actuate a first portion of the first catheter-based delivery system;
   a third actuator configured to be coupled to the first catheter-based delivery system; and
   a selector,
   wherein the first actuator is configured to actuate the third actuator such that a second portion of the first catheter-based delivery system is actuated,
   wherein the first actuator is configured to actuate the second actuator and the third actuator, and wherein when the selector is actuated the first actuator actuates one of the second actuator and the third actuator.

2. The apparatus of claim 1, wherein the motorized device is a motorized drill.

3. The apparatus of claim 1, wherein the apparatus is configured to limit the amount of translational motion of the second actuator by a limit switch.

4. The apparatus of claim 1, the apparatus further comprising a first catheter-based delivery system comprising
   a distal tip; and
   a capsule adjacent the tip;
   wherein the translational motion of the second actuator corresponds to translational motion of the capsule of the first catheter-based delivery system.

5. The apparatus of claim 1, wherein the apparatus further comprises a torque limiter, wherein the torque limiter is configured to limit an output torque of the apparatus.

6. The apparatus of claim 5, wherein the apparatus further comprises a gear box.

7. The apparatus of claim 1, the apparatus further comprising a first catheter-based delivery system comprising
   an inner sheath having a proximal end coupled to the second actuator,
   wherein the translational motion of the second actuator corresponds to translational motion of the inner sheath of the first catheter-based delivery system.

8. The apparatus of claim 7, wherein the first catheter-based delivery system further comprises an outer sheath surrounding the inner sheath, wherein the inner sheath is slidable relative to the outer sheath.

9. The apparatus of claim 1, the apparatus further comprising a first catheter-based delivery system comprising,
   a distal tip;
   an inner sheath having an inner sheath proximal end;
   an outer sheath having an outer sheath distal end and an outer sheath proximal end,
   wherein the first portion of the first catheter-based delivery system is the outer sheath such that the second actuator is coupled to the outer sheath proximal end,
   wherein the second portion of the first catheter-based delivery system is the inner sheath such that the third actuator is coupled to the inner sheath proximal end.

* * * * *